（12）United States Patent
Metelits

(10) Patent No.: US 9,707,366 B2
(45) Date of Patent: Jul. 18, 2017

(54) FLOW TRIGGERED PULSED OXYGEN DELIVERY FOR MEDICAL APPLICATIONS

(71) Applicant: Joel B. Metelits, Phoenix, AZ (US)

(72) Inventor: Joel B. Metelits, Phoenix, AZ (US)

(*) Notice: Subject to any disclaimer, the term of this patent is extended or adjusted under 35 U.S.C. 154(b) by 358 days.

(21) Appl. No.: 14/476,552

(22) Filed: Sep. 3, 2014

(65) Prior Publication Data

US 2015/0059764 A1 Mar. 5, 2015

Related U.S. Application Data

(60) Provisional application No. 61/943,610, filed on Feb. 24, 2014, provisional application No. 61/873,715, filed on Sep. 4, 2013.

(51) Int. Cl.
*A61M 16/20* (2006.01)
*A61M 16/06* (2006.01)
(Continued)

(52) U.S. Cl.
CPC .... *A61M 16/0677* (2014.02); *A61M 16/0051* (2013.01); *A61M 16/202* (2014.02);
(Continued)

(58) Field of Classification Search
CPC ..... A61B 5/0816; A61B 5/0836; A61B 5/097; A61B 5/6819; A61B 6/541; A61M 11/06; A61M 16/00; A61M 16/0051; A61M 16/0066; A61M 16/0069; A61M 16/04; A61M 16/0486; A61M 16/06; A61M 16/0666; A61M 16/0672; A61M 16/0677; A61M 16/0683; A61M 16/08; A61M 16/0816; A61M 16/085; A61M 16/10; A61M 16/101; A61M 16/1015; A61M 16/12; A61M 16/125; A61M 16/16; A61M 16/20; A61M 16/202; A61M 16/203;
(Continued)

(56) References Cited

U.S. PATENT DOCUMENTS 3,906,936 A    9/1975  Habal .......................... 128/2 R
4,278,082 A *  7/1981  Blackmer ......... A61M 16/0666
                                              128/207.18
(Continued)

FOREIGN PATENT DOCUMENTS

DE      19921917       12/2000   ............ A61M 16/00
WO      WO2013043504   3/2013    ............... A62B 9/02

OTHER PUBLICATIONS

International Preliminary Report on Patentability issued in related application No. PCT/US14/53924, dated Mar. 17, 2016 (5 pgs).
(Continued)

*Primary Examiner* — Annette Dixon
(74) *Attorney, Agent, or Firm* — Hayes Soloway P.C.

(57) ABSTRACT

A fluid delivery system provides fluid, such as supplementary oxygen, to a patient in response to inhalation. The fluid delivery system includes a valve assembly that is triggered by sensing nasal flow. The system includes a sensor configured to detect flow either directly through the nose and to detect any "flow leakage" through a patient's nasal cavity while mouth breathing. A method for conserved delivery of fluid to a patient that includes sensing such nasal flow is also provided.

19 Claims, 10 Drawing Sheets

(51) Int. Cl.
*A61M 16/00* (2006.01)
*A61M 16/10* (2006.01)

(52) U.S. Cl.
CPC ... *A61M 16/101* (2014.02); *A61M 2016/0018* (2013.01); *A61M 2016/0021* (2013.01); *A61M 2016/0027* (2013.01); *A61M 2016/0039* (2013.01); *A61M 2205/3368* (2013.01); *A61M 2205/3569* (2013.01); *A61M 2205/3592* (2013.01); *A61M 2205/8206* (2013.01)

(58) Field of Classification Search
CPC ........ A61M 16/207; A61M 2016/0021; A61M 2016/0024; A61M 2016/0027; A61M 2016/0036; A61M 2016/0039; A61M 2016/0042; A61M 2016/102; A61M 2016/1025; A61M 2202/0275; A61M 2202/03; A61M 2205/16; A61M 2205/3331; A61M 2205/3368; A61M 2205/3561; A61M 2205/50; A61M 2205/502; A61M 2205/52; A61M 2205/702; A61M 2205/8206; A61M 2205/8212; A61M 2205/8225; A61M 2209/08; A61M 2210/0625; A61M 2230/005; A61M 2230/205; A61M 2230/40; A61M 2230/42; A61M 2230/432; A61M 2230/63
USPC ............ 128/200.24, 202.22, 203.12, 203.25, 128/204.18, 204.21, 204.22, 204.23, 128/204.24, 204.26, 205.11, 205.12, 128/205.14, 205.17, 205.19, 205.23, 128/205.24, 205.25, 206.11, 207.14, 128/207.15, 207.18
See application file for complete search history.

(56) References Cited

U.S. PATENT DOCUMENTS

| | | | | |
|---|---|---|---|---|
| 4,706,664 A | * | 11/1987 | Snook | A61M 16/00 128/204.23 |
| 5,165,397 A | * | 11/1992 | Arp | A61M 16/00 128/204.21 |
| 5,485,850 A | * | 1/1996 | Dietz | A61B 6/541 128/204.23 |
| 5,694,923 A | | 12/1997 | Hete et al. | 128/204.18 |
| 5,865,174 A | * | 2/1999 | Kloeppel | A61M 16/00 128/204.21 |
| 6,612,307 B2 | | 9/2003 | Byrd | 128/204.26 |
| 7,013,898 B2 | | 3/2006 | Rashad et al. | 128/207.18 |
| 7,222,624 B2 | | 5/2007 | Rashad et al. | 128/204.23 |
| 7,866,320 B2 | * | 1/2011 | Nichols | A61M 16/0666 128/204.18 |
| 2003/0131848 A1 | | 7/2003 | Stenzler | 128/204.18 |
| 2003/0140924 A1 | | 7/2003 | Aylsworth et al. | 128/204.26 |
| 2004/0035422 A1 | | 2/2004 | Truitt et al. | 128/204.18 |
| 2005/0033247 A1 | | 2/2005 | Thompson | 604/275 |
| 2006/0169281 A1 | * | 8/2006 | Aylsworth | A61M 16/00 128/204.23 |
| 2007/0215156 A1 | | 9/2007 | Kwok | 128/204.21 |
| 2008/0236584 A1 | | 10/2008 | Holder | 128/204.23 |
| 2010/0116270 A1 | | 5/2010 | Edwards et al. | 128/201.21 |
| 2013/0092165 A1 | | 4/2013 | Wondka | 128/204.25 |

OTHER PUBLICATIONS

International Search Report and Written Opinion issued in related application No. PCT/US14/53924, dated Jan. 2, 2015 (10 pgs).

International Preliminary Report on Patentability issued in corresponding PCT patent Appln. No. PCT/US2012/055514 dated Mar. 25, 2014 (1 pg).

International Search Report and Written Opinion issued in corresponding PCT patent Appln. No. PCT/US2012/055514 dated Jan. 25, 2013 (9 pgs).

Palwai, A. et al. "Critical Comparisons of the Clinical Performance of Oxygen-conserving Devices" *American Journal of Respiratory Critical Care Medicine* 181(10): 1061-1071 May 15, 2010 (25 pgs).

European Search Report issued in application No. 14842330.0, dated Apr. 28, 2017 (9 pgs).

* cited by examiner

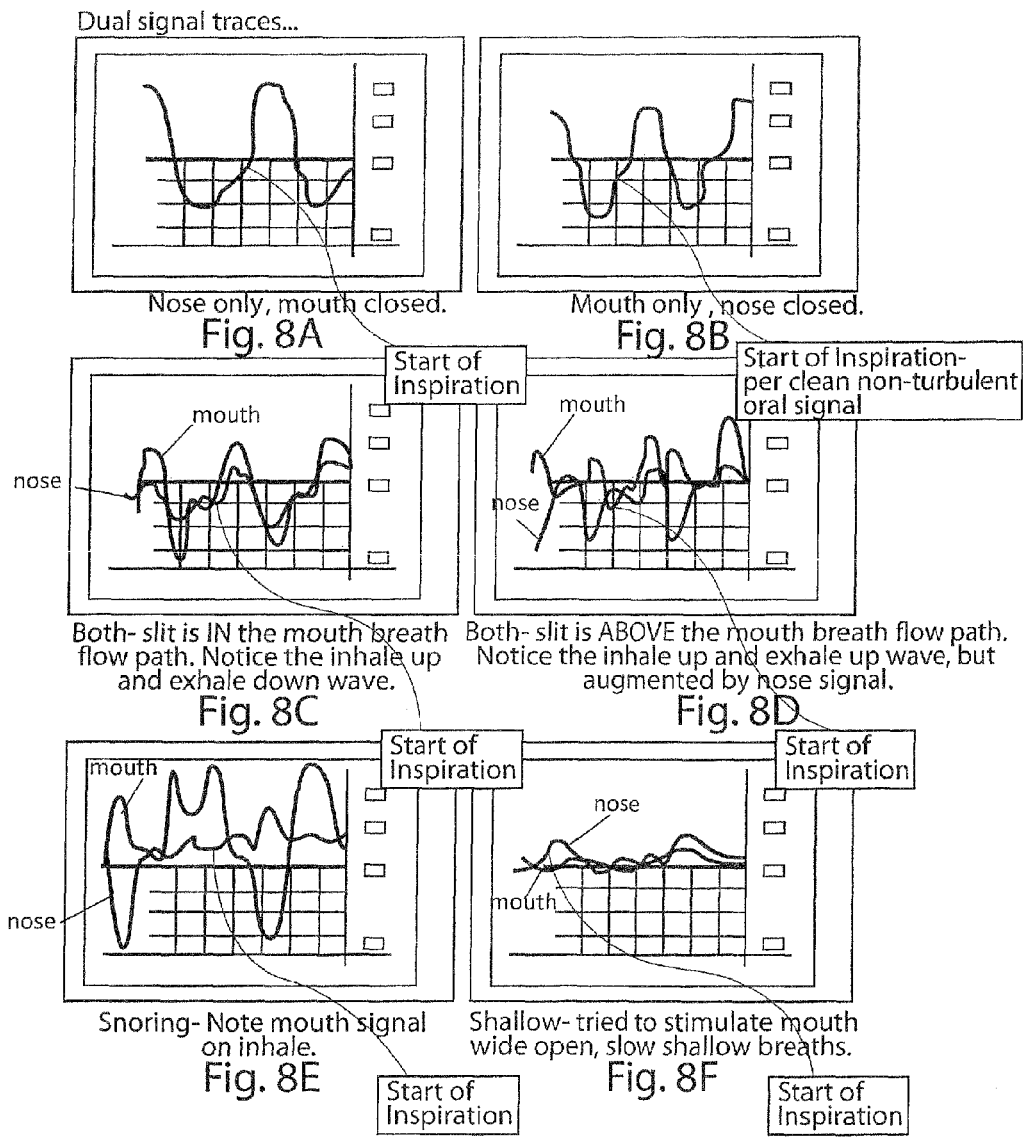

FLOW TRIGGERED PULSED OXYGEN DELIVERY FOR MEDICAL APPLICATIONS

CROSS REFERENCE TO RELATED APPLICATIONS

This application claims priority to U.S. Provisional Application No. 61/943,610, filed Feb. 24, 2014, and U.S. Provisional Application No. 61/873,715, filed Sep. 4, 2013, the contents of each of which prior applications are incorporated herein by reference.

FIELD OF THE INVENTION

The invention relates to devices and methods for monitoring and delivering oxygen to a patient, as well as for effectively conserving the delivery of oxygen to a patient.

BACKGROUND OF THE INVENTION

In the U.S. today approximately 1 million patients are receiving supplemental oxygen therapy through the Medicare payment system at a cost of approximately 2 billion dollars with this cost increasing annually at a rate of approximately 13% ("Long-term supplemental oxygen therapy." *Up-to-Date*; Jan. 18, 2013. Brian L Tiep, MD Rick Carter, PhD, MBA).

Most of the patients receiving long term supplemental oxygen therapy (LTOT) suffer from chronic hypoxemia as a result of having a chronic obstructive pulmonary disease (COPD). Presently there is no cure for this condition. However the detrimental impact of chronic hypoxemia may be mitigated by the administration of long term oxygen therapy (LTOT). The continuous inhalation of low flows of oxygen, typically 2-3 lpm (liter per minute), from a nasal cannula increases the concentration of oxygen that the patient is breathing. It is estimated that for each 1 lpm flow, the overall inhaled concentration rises by 3-4%. The increase in oxygen concentration compensates for the poor function of the patient's lungs in absorbing oxygen.

Generally when a patient is diagnosed with chronic hypoxemia, oxygen is prescribed at a fixed flow rate based on a 20-minute titration test in the doctor's office. During the test, the patient's blood oxygen saturation is measured by either using an invasive blood gas analyzer or a non-invasive device such as a pulse oximeter. While measuring the blood saturation ($SpO_2$), the patient may be asked to walk on a treadmill so as to measure his or her need for supplemental oxygen while exerting him or herself. Based on this brief test, a fixed flow of oxygen is prescribed. The patient may be advised to increase the flow rate of oxygen during exertion, for example, while climbing stairs, while sleeping or if they feel short of breath. The patient will need confirmation of the adequacy of oxygen treatment, with the goal of keeping the patient's oxygen saturation above 90% during all of their activities, including during sleep. Some patients may be prescribed oxygen to breathe 24 hours per day or may only require oxygen while ambulating or may need oxygen treatment only when sleeping. Among patients requiring LTOT during their waking hours, often higher flow rates are required while sleeping. It is common practice to increase the flow rate by 1 liter per min while a patient is sleeping.

If a patient needs to breathe oxygen even while resting, he or she will be given a stationary oxygen generating unit in his or her home which can be set to produce, e.g., up to 5 lpm of 93% oxygen. Generally, the units today are manually set to a prescribed flow rate in liters per minute. If a patient requires oxygen while ambulating, he or she typically will carry small high pressure oxygen cylinders or small refillable liquid oxygen dewars. Small portable oxygen generators are also available which can produce up to 3 liters per minute of continuous oxygen or deliver pulsed oxygen at higher flow rates. These portable oxygen delivery systems all have drawbacks. Portable concentrators are usually bulkier and noisier and have a relatively short battery life. The small high pressure oxygen cylinders have restricted capacity, especially the smaller ones, but do not need a battery or make the kind of noise produced by the concentrators.

Due to the expense of providing oxygen in small cylinders and dewars for ambulation, various oxygen conserving devices have been developed to conserve the oxygen flow. These prior art oxygen conserving devices only deliver short pulses of oxygen at the beginning of a patient's inhalation. By not delivering oxygen during exhalation or the later period of inhalation, the oxygen which would have had no impact on increasing the patient's oxygen saturation is conserved. There now exists both pneumatic and electronic oxygen conserving devices which claim to achieve oxygen conserving ratios from 2:1 to 7:1 compared to the delivery of continuous oxygen flow. The higher conservation ratios are achieved by the electronic devices which are programmed to skip breaths so that oxygen pulse is only delivered every other breath. However, electronic devices cannot be used on all ambulating patients since their high conservation ratios can actually result in poor oxygen saturation for the patient particularly during periods of increased oxygen utilization as in walking vigorously or walking up stairs.

Moreover, currently available conserving devices measure a drop in nasal air pressure, which for most patients is inadequate to trigger the release of oxygen under various circumstances, including: extremely reduced respiratory function; most mouth breathing; talking while walking; while walking briskly or while talking intensely; or while sleeping. Upon initiation of these ambulatory devices, patients are "taught" to focus on nasal breathing to help trigger the device. Often a patient needs to stop his or her activity and focus on his or her nasal breathing, or to put the nasal cannula probe in his or her mouth to more effectively trigger the device.

Pressure sensing of the onset of inhalation in electronic oxygen conservers is currently accomplished in one of two ways:
1. Some prior art designs employ a dual lumen cannula in which one of the lumens is dedicated to pressure sensing while the other is dedicated to the supply of oxygen. This design is meant to be more sensitive to the onset of inhalation but suffers from the drawback of only being able to deliver oxygen to one of the nasal passages.
2. Other designs use a single lumen cannula that typically has a pressure sensor connected to a T piece below the two nasal prongs. Overall pressure drop associated from inhalation is sensed from both nasal passages and oxygen is then delivered to both nasal passages.

Both designs suffer from the drawback that if one of the patient's nasal passages is blocked, it will interfere with the detection and delivery of oxygen.

Another flaw with current oxygen generating systems is the fact that a patient's ideal need for oxygen varies with time both in the short term as a result of varying exertion and in the long term as a result of improvement or deterioration in health. When a doctor prescribes a fixed flow rate of oxygen for a patient, the doctor is mainly concerned with ensuring that the patient's blood saturation does not drop below an oxygen saturation of 88-89%. The doctor does not want to have a patient experience desaturation of oxygen below 90% during any of the patient's activities. Although there exist theoretical concerns about potential toxicities in patients administered oxygen in high concentrations (above 50 percent) for extended time periods (e.g., absorptive atelectasis, increased oxidative stress, and inflammation), clinical experience has provided little support for these concerns in the setting of LTOT. ("Long-term supplemental oxygen therapy." *Up-to-Date*; Jan. 18, 2013. Brian L Tiep, MD Rick Carter, PhD, MBA).

Current oxygen treatment plans are prone to error as proved by a study by Fussell et al. (*Respiratory Care*. February 2003, Vol. 48 No. 2). In that study, blood saturation levels of 20 patients suffering from COPD were monitored continuously using pulse oximetry to confirm if each patient's oxygen prescription adequately maintained his or her saturation. The conclusion of the study was that there was a poor relationship between conventional oxygenation assessment methods and continuous ambulatory oximetry during LTOT screening with COPD patients. More recently in an article entitled "Critical Comparisons of the Clinical Performance of Oxygen-conserving Devices," Am. J. Respir. Crit. Care Med. 2010 May 15; 181(10): 1061-1071, the current collection of conserving devices all based on pressure sensing were criticized as failing to deliver on their efficacy claims. The authors claimed that "Although each device activated during nose and mouth breathing, none consistently performed according to engineering expectations."

When a patient obtains low oxygen saturation results while using conserving devices or fixed oxygen flow rates, the natural response is to simply increase the flow rate. Increased nasal flow rates become increasingly expensive and are generally not well tolerated. Some COPD patients who use stationary oxygen concentrators in their homes are financially impaired and are concerned about the power costs of continuously running an oxygen concentrator. In many cases this has led to a compliance issue where the patient may elect to not switch on the concentrator and follow the therapy as prescribed by the doctor in order to save on their electricity bill. Moreover, these oxygen concentrators throw a fair amount of heat into the room, which may further add to energy costs, i.e., for cooling the room. Current oxygen concentrator designs typically will produce a maximum flow rate, e.g., of 5 lpm. If a patient's resting prescription is 2 lpm, the patient may set a flow rate through their cannula to the required flow and the excess oxygen that is being produced is simply pushed into the nostrils which while mouth breathing may be wasted. Many oxygen therapy patients can spend a significant amount of their time while active, or talking, or napping, or sleeping with blood oxygen saturation levels that are unacceptable.

Certainly pressure-based oxygen conserving units fail to live up to their claims when mouth breathing during more vigorous activity, while talking, while eating and/or when sleeping. Often patients on ambulatory oxygen will have to stop and focus on their nose breathing, or put the nasal cannula prongs in their mouth and suck on them to trigger the release of oxygen. When oxygen needs are not being met, the simple solution is to increase the nasal flow rate, which causes increasing problems of uncomfortable nasal passage drying and sometimes nasal mucosal bleeding. Further, patients often stop their oxygen delivery system altogether when eating.

It is therefore an object of the present invention to provide a new and improved type of conserving oxygen regulator which can be used to efficiently and effectively oxygenate a patient that overcomes the aforesaid and other disadvantages of the prior art. Another object of the invention is to provide a new and improved type of conserving oxygen regulator that can be used as a standalone regulator or "piggyback" onto non-conserving regulators to make them efficient. Yet other objects of the invention are to provide a new and improved type of conserving oxygen regulator that can be incorporated in all currently used conserving oxygen generators and can be applied to multiuser hospital or clinic liquid oxygen systems to add efficiency. This invention can also allow for pulse oxygen use during sleep apnea treatment with C-PAP or Bi-PAP machines.

SUMMARY OF THE INVENTION

The following brief summary is not intended to include all features and aspects of the present invention, nor does it imply that the invention must include all features and aspects discussed in this summary.

The present invention provides improvements over the aforesaid prior art devices by providing a nasal cannula or a combined nasal and oral cannula with a valve assembly and a flow sensor for sensing "flow leakage" through a patient's nasal cavity. This "hidden signal," coupled with simultaneous monitoring of nasal and/or oral flow patterns, enables a truly on-demand oxygen delivery system without uncertainty or misdirected oxygen—both of which lead to oxygen wastage, or inadequate oxygen delivery to the patient.

Accordingly, in one embodiment the present disclosure provides a fluid delivery system comprising at least one source of fluid; at least one valve assembly coupled to said at least one source of fluid, wherein the at least one valve assembly is configured to allow flow of fluid from the at least one source during patient inspiration; an outlet end comprising a nasal or oro-nasal cannula in fluid communication with the at least one valve assembly; and a nasal flow sensor for triggering fluid delivery in response to patient inspiration.

The fluid delivery system may further comprise a power source configured to operate the at least one valve assembly. The location of the nasal flow sensor may be in or adjacent the nasal cannula or oro-nasal cannula, adjacent the fluid source, or in air tubing between the nasal cannula or oro-cannula and the at least one source of fluid.

In an embodiment in which the fluid delivery system comprises an oro-nasal cannula, the oro-nasal cannula may comprise split nasal cannuli and an oral cannula. The split nasal cannuli and the oral cannula may be couple to one another, and said coupling may be achieved by an adjustable length sleeve or by detachable tubing. Furthermore, the split nasal cannuli and the oral cannula may be in fluid communication with a shared valve assembly or each may be in fluid communication with a separate valve assembly. The fluid delivery system may further comprise an oral flow sensor for triggering fluid delivery in response to patient inhalation.

The at least one valve assembly of the fluid delivery system of the present disclosure may comprise at least one solenoid valve. Further, the nasal flow sensor may be configured to detect flow through a patient's nasal cavity, both during nasal inhalation as well as to detect "nasal flow leakage" during mouth inhalation. In a preferred embodiment, the fluid delivered by the fluid delivery system is supplement oxygen. The fluid delivery system may further comprise circuitry for controlling the at least one valve assembly based on signals from the flow sensor. The circuitry may comprise a trigger mechanism for actuating the release of fluid through the at least one valve assembly.

In another embodiment, the present disclosure provides an apparatus for conserving oxygen being delivered from an oxygen supply to a patient, comprising: an oxygen conserver controller connected between the oxygen supply and a nasal cannula or an oro-nasal cannula, wherein said controller comprises at least one valve triggered selectively to deliver oxygen to the nasal or oro-nasal cannuli; a sensor configured to sense nasal inspiration; and a trigger mechanism, communicating with said sensor for actuating the conserver controller, wherein the sensor for sensing patient inhalation is configured to detect flow through a patient's nasal cavity, both during nasal inhalation as well as to detect "nasal flow leakage" during mouth inhalation.

In yet another embodiment, the sensor of the apparatus may be selected from the group consisting of an acoustic sensor, a flow sensor, a pressure sensor, a temperature sensor, a carbon dioxide sensor, a strain gauge, and an electro-mechanical sensor. Further, the sensor and the trigger mechanism may be remote from each other and may also communicate either by wire or wirelessly.

The present disclosure further provides a method for conserved delivery of fluid to a patient, comprising the steps of: providing a valve in communication with a fluid source and a nasal or oro-nasal cannula; sensing, with a nasal flow sensor in communication with the valve, nasal flow during nasal inspiration or in the form of "nasal flow leakage" that occurs when the patient is mouth breathing; and triggering the valve, in response to the sensed inspiration or leakage, to release fluid from the fluid source for delivery to the patient via the nasal or oro-nasal cannula. The fluid delivered by the method may comprise oxygen.

BRIEF DESCRIPTION OF THE DRAWINGS

The invention will be better understood from a reading of the following detailed description taken in conjunction with the drawings in which like reference designators are used to designate like elements, and in which:

FIGS. 8A-8F are graphs illustrating oxygen flow as sensed in accordance with the present invention.

DETAILED DESCRIPTION OF THE PREFERRED EMBODIMENTS

Figure 1:
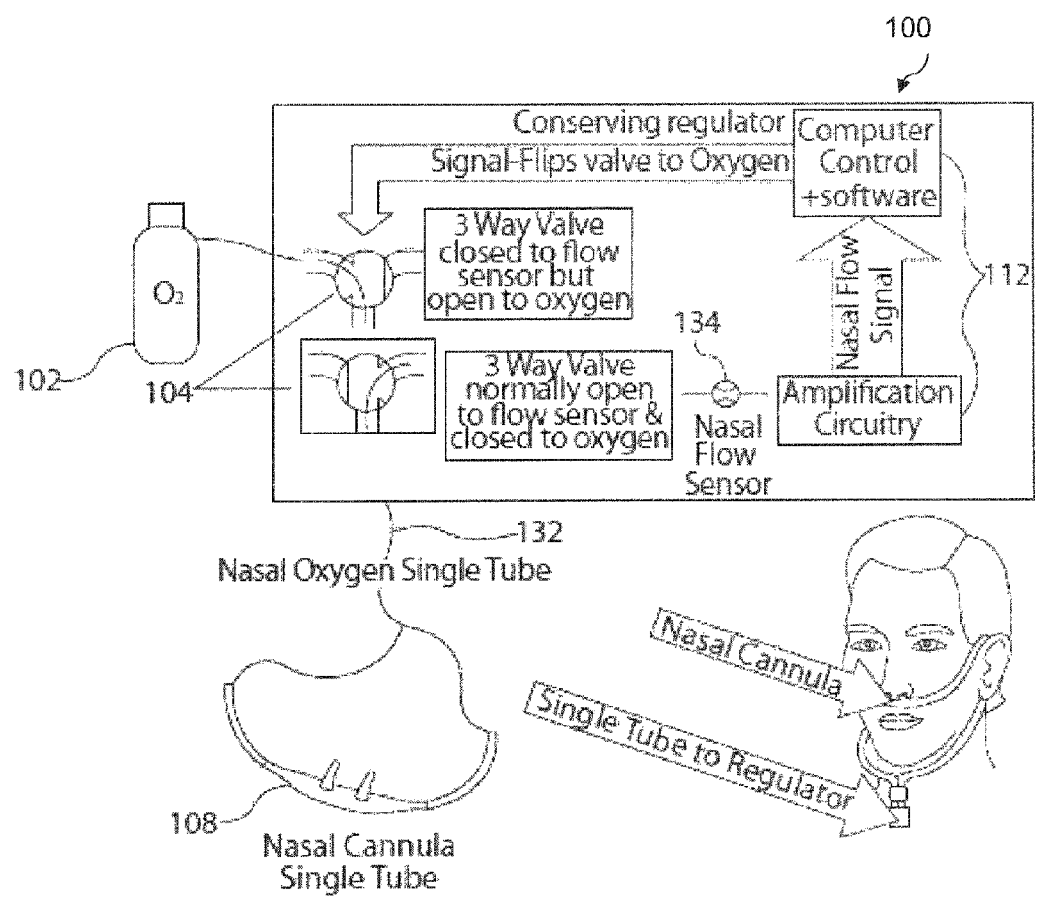
FIGS. 1-3 are block diagrams of three different systems for fluid delivery in accordance with the present invention.

Embodiments are described in the following description with reference to the drawing figures in which like numbers represent the same or similar elements. Reference throughout this specification to "one embodiment," "an embodiment," "certain embodiments," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The fluid delivery system of the present invention provides oxygen, to a patient in intermittent time intervals, based on the patient's tidal breathing. The fluid delivery system includes a nasal or oro-nasal flow-triggered valve assembly that opens in response to a patient's inhalation, and closes during the inspiratory phase to conserve oxygen which would otherwise be wasted on filling up a patient's "dead space" prior to the end of inhalation. That is to say, the present invention senses "flow leakage" through a patient's nasal cavity, on inspiration, through a nose flow sensor placed in a nasal cannula or along the path from the nasal tab to the regulator, and triggers the regulator valve to open and close in synchrony with the patient's tidal breathing.

The nasal flow sensor is sensitive enough to sense the "flow leakage" through the nasal passage while a patient is mouth breathing. With very sensitive flow sensors, a patient with at least one nostril not totally obstructed has enough "flow leakage" through his or her nasal cavity even when breathing through his or her mouth to provide a clear definition of precisely when inspiration and expiration begins. This "hidden signal," alone, or coupled with simultaneous monitoring of oral and nasal flow patterns, enables a truly on-demand oxygen delivery system without uncertainty or misdirected oxygen—both of which lead to oxygen wastage or inadequate oxygen delivery to the patient. With this flow information, the risk involved, for example, in trying to treat a mouth breather who is sleeping with pulse regulated oxygen as opposed to continuous flow oxygen is eliminated. Similarly, an ambulatory patient who begins mouth breathing, no longer needs to pause, and "catch his breath" by conscious deliberate nasal breathing. Thus, while using this device, a patient has a pleasing sense of synchrony between breath initiation and delivery of oxygen and, by eliminating any perceptible delay in oxygen delivery, feels free to move about and talk spontaneously without fear of missing his or her oxygen pulse. At long last the efficiency of conserving devices can be utilized in hospitalized or bedridden patients from a central liquid supply with a reliable pulse oxygen delivery system.

Moreover, unlike pressure sensors described in the prior art, sensing and thus triggering is essentially instantaneous. Thus, there is essentially no delay delivering supplemental oxygen. Nor is there any waste of oxygen compared to conventional flow-sensor detectors. Consequently, the flow of supplementary oxygen is turned on and off in concert with the patient's tidal breathing. As a result, supplementary oxygen is conserved because the supplementary oxygen is not provided when the patient does not need the oxygen: during the filling of "dead space" (i.e., the volume of air which is inhaled that does not take part in the gas exchange), or during exhalation.

As used herein, inhalation is used synonymously with inspiration, and exhalation is used synonymously with expiration. Inhalation is the movement of air from the external environment, through the airways, and into the lungs. During inhalation, the chest expands and the diaphragm contracts downwardly or caudally, resulting in expansion of the intrapleural space and a negative pressure within the chest cavity. This negative pressure results in airflow primarily from either the nose or the mouth into the pharynx (throat) and trachea, eventually entering the lungs. However, even when mouth breathing, a patient still experiences at least a small amount of airflow through the nose. I have found that even a small amount of airflow is sufficient to trigger the nasal flow sensor. Moreover by using a nasal flow sensor the determination of inspiration is essentially instantaneous, taking advantage of the most important phase of inspiration to deliver oxygen. Although any bolused or pulsed oxygen delivery system is set as a flow rate equivalent, there is more consistency and parity with bolus amounts and continuous flow rates. The term "pulse equivalent" which is presumed comparable to continuous flow is how current conserving regulators are set. Continuous flow rates are set at liters per minute.

Since pulse units do not put out continuous oxygen, they cannot be measured in liters per minute. Instead, they are classified by size of the individual pulse (bolus), i.e., how often that pulse can be delivered in a minute, and when the pulse is delivered in the inspiratory (breathing) cycle. The other issue for pulsed oxygen concentrators which can be limiting is when a patient tries to take more breaths per minute than the unit is capable of producing. When this occurs, the oxygen user will either get a smaller pulse, a pulse with less oxygen, or no pulse at all. In a situation where the oxygen user exerts and become significantly out of breath, the unit may fail to meet the user's needs. With a nasal flow sensor in accordance with the present invention, I am able to get closer to the equivalent of continuous oxygen flow since the oxygen is delivered essentially immediately (i.e., generally within milliseconds of the initiation of inhalation after the user begins to inhale air). Without the delay inherent in the pressure sensor method of triggering oxygen release there is no need to push up the bolus amount to make up for the delay in delivery.

Also using nasal flow triggered pulse oxygen in accordance with the present invention, the user does not have to think how he or she is breathing—the trigger senses inspiration through the nasal flow sensor even when the patient is mouth breathing or while talking, walking and talking, or eating. It does not matter if the user has large nostrils or if the user is dozing in a chair, or sleeping. There is no required training—the user just places the cannula in his or her nostrils and experiences essentially synchronous oxygen delivery. Pressure-triggered pulse oxygen delivery has a noticeable delay in the "puff" of oxygen delivered, while nasal-flow-triggered oxygen delivery has essentially no perceivable delay, giving it a more natural feel. It releases the oxygen essentially as the user is inhaling not after the user starts inhaling. By way of comparison, when using a conventional chest strain gauge to judge inhalation, the current nasal flow sensor triggered opening of the solenoid happens before any chest motion is detected! This improved synchronicity between inhalation and oxygen delivery is more comfortable, more efficacious and more reliable, and since it actually performs what other types of conserving units only claim to do, will yield better patient compliance.

Nasal flow triggered oxygen also can use volume analysis to determine when a patient is mouth or nose breathing. Thus, while sleeping, the present invention can be used to change the delivery of the oxygen delivery from strictly nasal at low flow rates to nasal and oral oxygen delivery when a patient requires higher flow rates. This could be accomplished with a dual nasal-oral oxygen cannula to deliver larger volumes incapable of being pulsed through the nose. With pressure-triggered pulse delivery that is currently available, high-flow oxygen delivery via pulsed delivery is not possible.

Additional uses of this clinically insignificant trivial nasal flow during mouth breathing are in the diagnostic field of sleep disorders. Much attention has been directed toward sleep studies to confirm the diagnosis of sleep apnea, which is being diagnosed both in sleep labs and home sleep studies. The sensing and documentation of breathing during sleep can be enhanced by measuring inspiratory flow more accurately. Thus the same nasal flow sensor which can trigger pulse oxygen delivery can also be adapted to efficiently measure breathing during diagnostic evaluations. Patients who have sleep apnea or periodic breathing and are only using oxygen supplementation can also use pulsed oxygen delivery safely. This device can now allow patients who use C-PAP or Bi-PAP machines to take advantage of the efficiency benefits of pulsed oxygen delivery—delivering the oxygen to the nasal passage during inspiration. This is an improvement over the current method of just adding oxygen to the hose traveling to the mask, which provides a most inefficient oxygen delivery system given the built-in mask venting as well as the inadvertent mask leaks which occur during the night.

Nasal-flow-triggered oxygen delivery also can free up traveling patients who are currently limited to 3 liters per min continuous flow rates. With portable concentrators, setting a pulse rate of 4-6+ liters per min while sleeping is just not reliable ("Critical Comparisons of the Clinical Performance of Oxygen-conserving Devices," Am. J. Respir. Crit. Care Med. 2010 May 15; 181(10): 1061-1071; Published online 2010 Feb. 4. doi: 10.1164/rccm.200910-1638OC PMCID: PMC2874449). These pulsed high flow devices claim to be able to oxygenate patients while sleeping, but most healthcare providers do not consider pulsed high flow devices to reliably deliver sufficient oxygen to sleeping patients.

Nasal-flow-triggered oxygen delivery also can be adapted to "piggyback" onto hospital and clinic central liquid oxygen systems at the point of delivery, providing efficiency where none exists currently.

Figure 2:
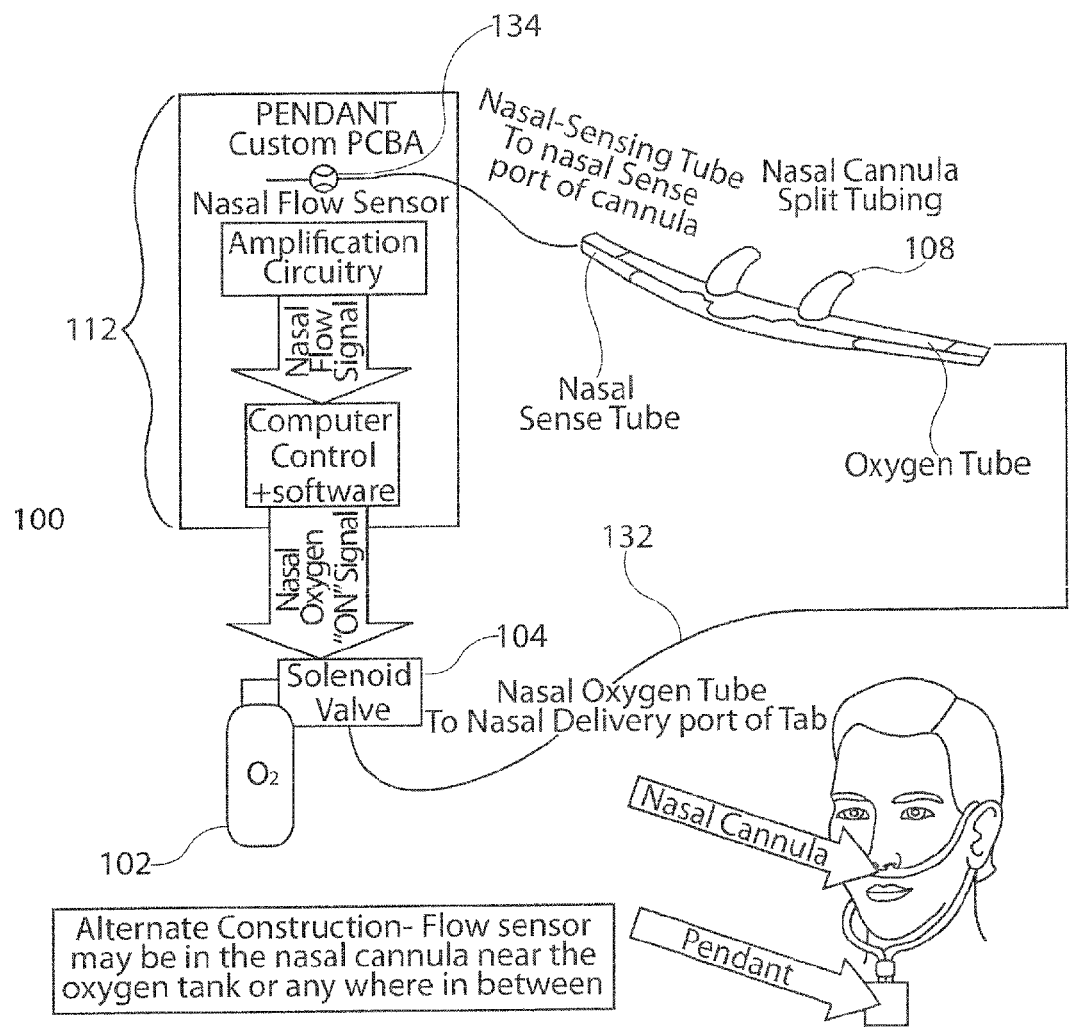
Figure 3:
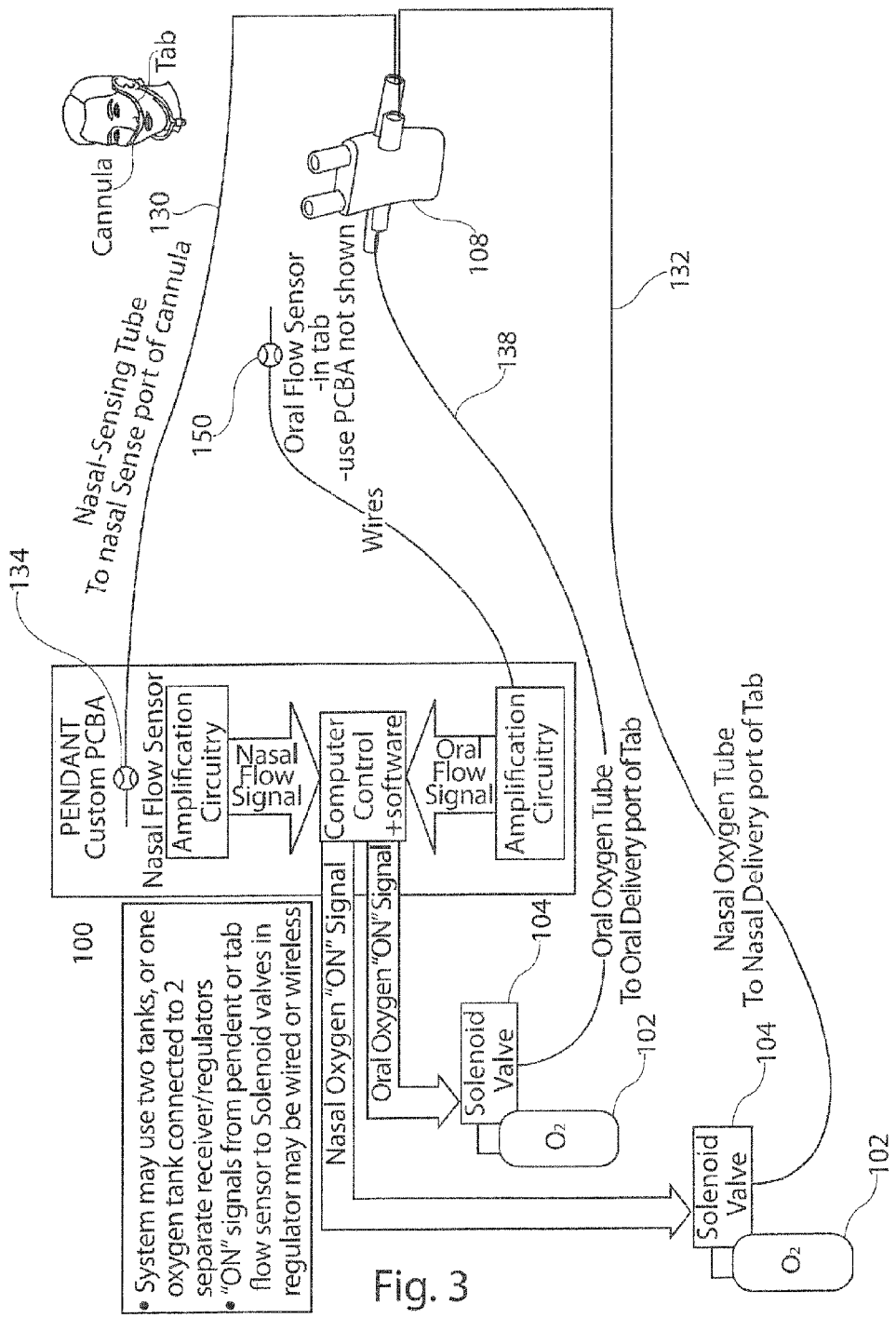

Referring to FIGS. 1-3, the fluid delivery system 100 of the present invention comprises a fluid source such as an oxygen supply tank 102 and a fluid regulator 104 coupled to the fluid source 102. The invention may comprise more than one fluid source 102 and/or more than one fluid regulator 104, as shown in FIG. 3. Examples of fluid sources 102 include, for example: an oxygen generation apparatus, a stationary oxygen reservoir within a hospital setting, or a portable canister of pressurized oxygen or a liquid oxygen dewar. The fluid delivery system 100 further includes a power source, such as a battery or utility power (not shown), and electronics controls including a flow sensor, amplification circuit and software, indicated generally at 112. As shown in FIG. 1, the electronics controls may be located at any position between the fluid source 102 and an outlet end such as a nasal cannula or an oro-nasal cannula 108, including adjacent fluid source 102 or adjacent outlet end 108. Additionally, as shown in FIGS. 2-3, the electronics controls may be located in a pendant in communication with the outlet end.

The fluid regulator 104 is in fluid communication with the fluid source 102, as well as the outlet end 108. Such fluid communication may be facilitated by, for example, tubing connecting or coupling the fluid regulator to the fluid source and outlet end. The fluid regulator 104 discontinues oxygen flow at a predetermined pressure at the outlet end 108. Outlet end 108 may comprise a nasal cannula, as shown in FIGS. 1-2, or may comprise an oro-nasal cannula, as shown in FIG. 3. Preferably, the fluid regulator 104 includes a dual pressure gauge that measures inlet pressure at the source (e.g., oxygen left in the fluid source), and outlet pressure at the outlet end.

The fluid regulator 104 comprises a solenoid valve which opens the flow of oxygen to the nasal or oral-nasal tab for a predetermined amount of time and sends a pulse of oxygen to the outlet end 108, based on data from the flow sensor. When the outlet end comprises an oro-nasal cannula, as depicted in FIG. 3, the fluid regulators 104 are solenoid valves which open the flow of oxygen to the oral-nasal tab for a predetermined amount of time and send a pulse of oxygen either to the nose or mouth, based on data from the flow sensors which define which orifice (nose or mouth) is "requesting" the clearest flow to the lungs. This determination is based on separate sensors monitoring flow—one in the nasal path and one in the oral path.

Rather than sensing a pressure drop as the trigger (either mechanical or electronic), this invention senses essentially instantaneous nasal flow to trigger a solenoid valve. The opening and closing of the oxygen source can then deliver a precise "timed" pulse of oxygen strategically placed for releasing oxygen to the user. This device essentially converts any regulator into a "smart" conserving regulator. Various safety aspects in this "smart" conserving regulator nasal or oro-nasal cannula system can be built-in, for example: self-testing the solenoids and sensors and power supply; detecting an inadequate oxygen source; detecting a failure of oxygen flow to the cannula, e.g., if there is tube separation or the tube pinched; defaulting to continuous flow, e.g., if the system is not operating properly; and detecting any flow sensor or oxygen channel obstruction. As will be described below in greater detail, the fluid regulator 104 triggers a valve, e.g., a pressure valve assembly, to open at patient inhalation for a set amount of time, e.g., approximately 400 ms.

Figure 4:
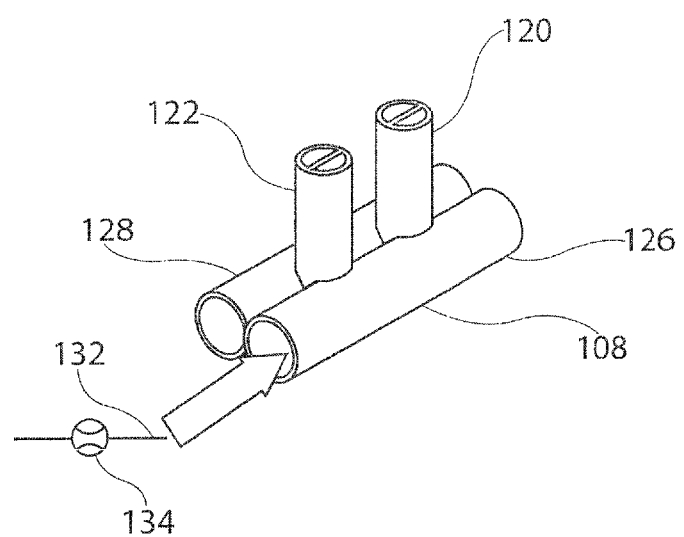
FIG. 4 is a simplified view of a nasal cannula and nasal flow sensor in accordance with the present invention.
Figure 5A:
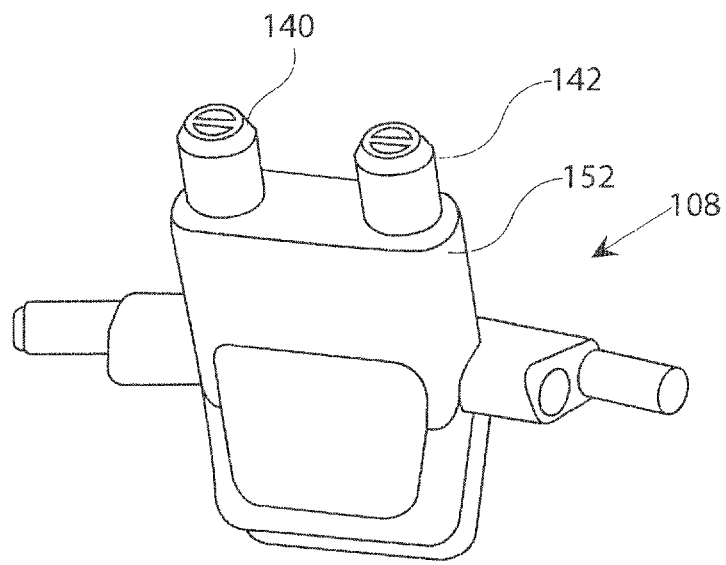
FIGS. 5A-5D are perspective views showing various embodiments of oro-nasal cannuli in accordance with the present invention.
Figure 5B:
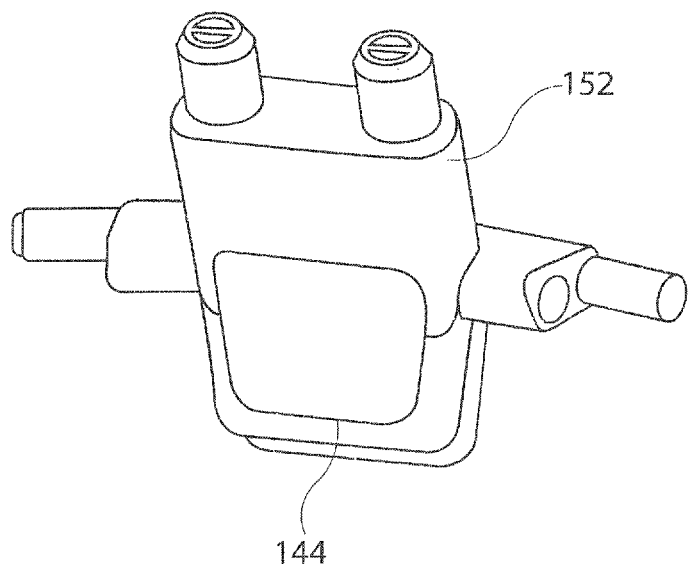
Figure 5C:
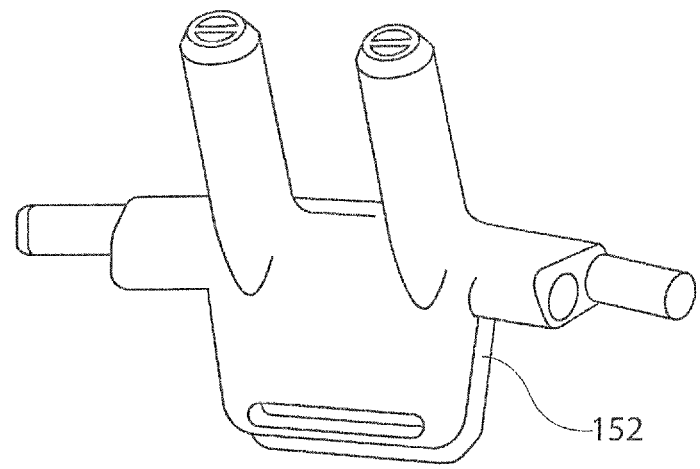
Figure 5D:
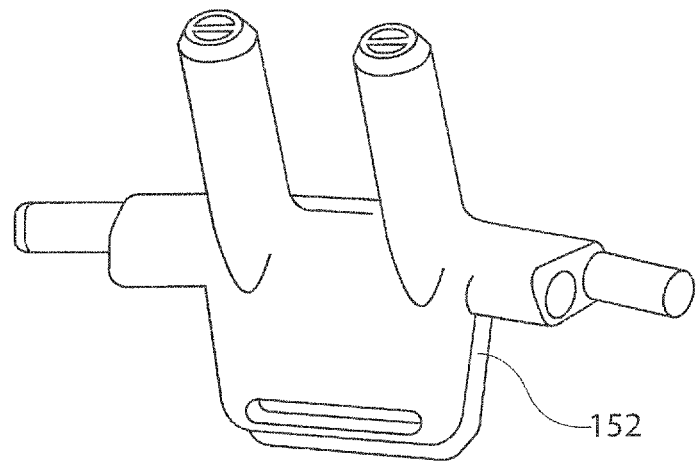
Figure 6:
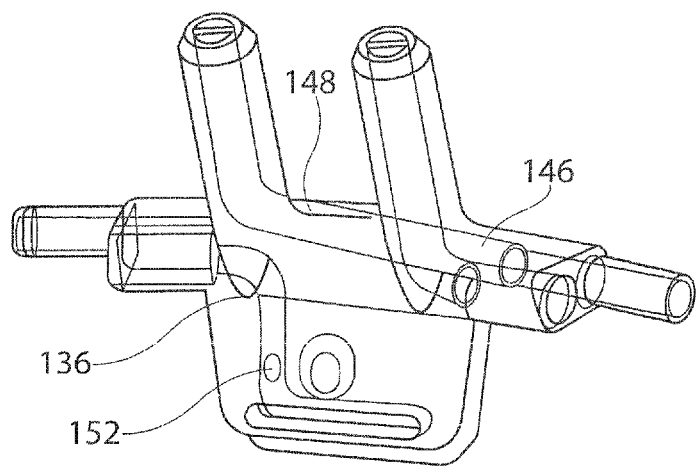
FIG. 6 is an X-ray view of the oro-nasal cannula of FIG. 5A.

Referring to FIG. 4, outlet end 108 may comprise a cannula comprising a hollow body having two nasal cannuli 120 and 122 extending therefrom. Nasal cannuli 120, 122 are connected through split tube conduits 126 and conduit 128 to nasal oxygen tube 132 which is connected through solenoid valve 104 to oxygen source 102 (FIGS. 1 and 2). A nasal flow sensor 134 preferably is incorporated into one of the nasal cannuli 120, 122. Alternatively, the nasal flow sensor 134 may be located adjacent the oxygen source, or anywhere in between.

Referring also to FIGS. 5A-5D and FIG. 6, outlet end 108 may alternatively comprise an oro-nasal cannula comprising a hollow body having two nasal cannuli 140 and 142 extending therefrom and an oral cannula 144. Nasal cannuli 140, 142 are connected through split tube conduits 146 and conduit 148 to nasal oxygen tube 132 which is connected through solenoid valve 104 to fluid source 102. A nasal flow sensor 134 as will be described in detail below, preferably is incorporated into one of the nasal cannuli 140, 142.

In like manner, the oral flow cannula is connected via flow passage 136 and conduit 138 to the fluid source 102 via valve 104. An oxygen flow sensor 150 preferably is incorporated into flow passage 136. Referring again to FIGS. 5A-5D, in order to accommodate different patients, the oro-nasal cannula 108 may include various length philtrum spacers 152. Further, the nasal cannuli and the oral cannula of the oro-nasal cannula may be coupled to each other, e.g., via detachable tubing or an adjustable-length sleeve.

Figure 7A:
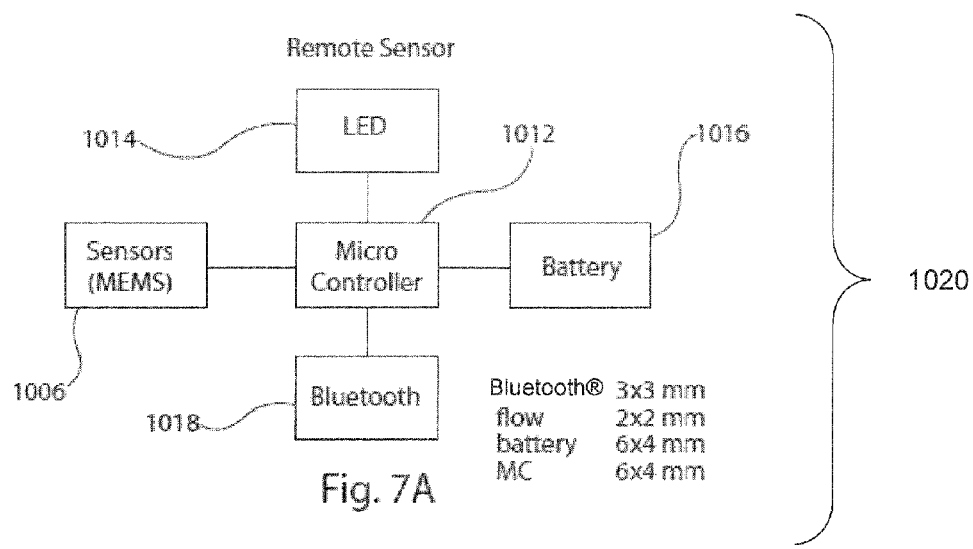
FIGS. 7A and 7B are block diagrams of a remote sensor and trigger mechanism in accordance with a preferred embodiment of the present invention.
Figure 7B:
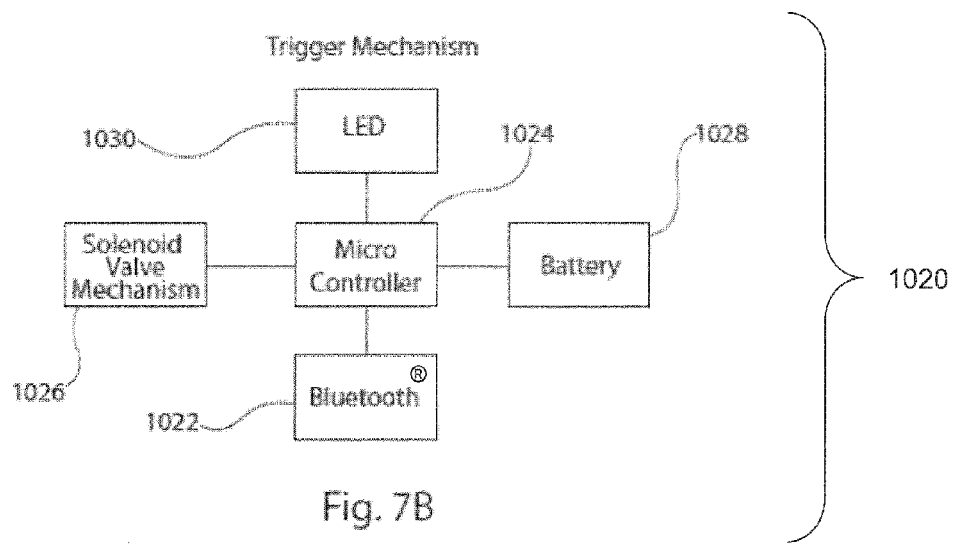

Referring to FIGS. 7A and 7B reference number 1006 represents a sensor designed to measure infinitesimal flow in the nose 1006 and through microprocessor or microcontroller 1012, both battery powered 1016, which will communicate with the trigger mechanism (FIG. 7B). Sensor 1006 preferably comprises a very fast flow measurement such as a Microflow Sens MFS02 sensor manufactured by Innovative Sensor Technology of Wattwil, Switzerland. Various possible communications between the trigger amplifier and the conserving regulator, for example, the system may be hard wired or it may be wireless using, for example, a Bluetooth® communicator or other wireless communicator which would turn on an LED when the battery weakens enough to risk failure to sense efforts of breathing or delivery of oxygen.

An LED 1014 preferably is included to signal that the sensor is on and that the battery 1016 has sufficient charge. The microprocessor 1012 receives signals from sensor 1006, and transmits the signals via a transmitter 1018 to trigger mechanism (FIG. 4B). The trigger mechanism includes a receiver 1022 which communicates with microprocessor or microcontroller 1024 for sending signals to a solenoid valve mechanism 1026. The trigger mechanism preferably includes a battery 1028 and an LED 1030 for signaling when the trigger mechanism is activated and that the battery has sufficient charge.

The remote sensor and trigger mechanism may be hard wired, e.g., by incorporating wires into the tubing, connecting the sensor and trigger mechanism and the oxygen supply, or can be designed to communicate wirelessly, for example, using Bluetooth® short-wave length radio transmission technology or other wireless protocol. Thus the sensor and trigger mechanism may be adjacent each other or remote from each other.

Any sensor or combination of sensors that can be used to measure or identify the difference in properties between and inhalation and exhalation maneuver that can be used to synchronize and turn the conserving regulator on and off. Examples of sensors that may be used to detect patient inhalation/exhalation include air flow sensors, air pressure sensors, temperature sensors that measure a temperature difference between the inhaled and exhaled breath, carbon dioxide gas sensors that measure the gas component level between the inhaled and exhaled breath, and also physical measurement systems such as strain gauge chest straps to measure the expansion and contraction of a patient's chest cavity. Other sensors such as acoustic sensors that detect the sound of inhalation and exhalation flow such as described in U.S. Published Application No. 2005/0183725 or in U.S. Pat. No. 6,152,130 advantageously may be employed. Yet another possible sensor comprises an electro-mechanical sensor having a moveable vane capable of being displaced when air flow is generated by patient inhalation, for example, following the teachings of U.S. Pat. No. 5,655,523.

Referring to FIGS. 8A-8F, shown are graphs which depict the inspiration phase and the expiration phase of the respiratory cycle of a patient under various conditions assessed by the sensor of the present invention, and illustrating how the flow data may be used to trigger oxygen flow from a supplementary oxygen supply.

Figure 9:
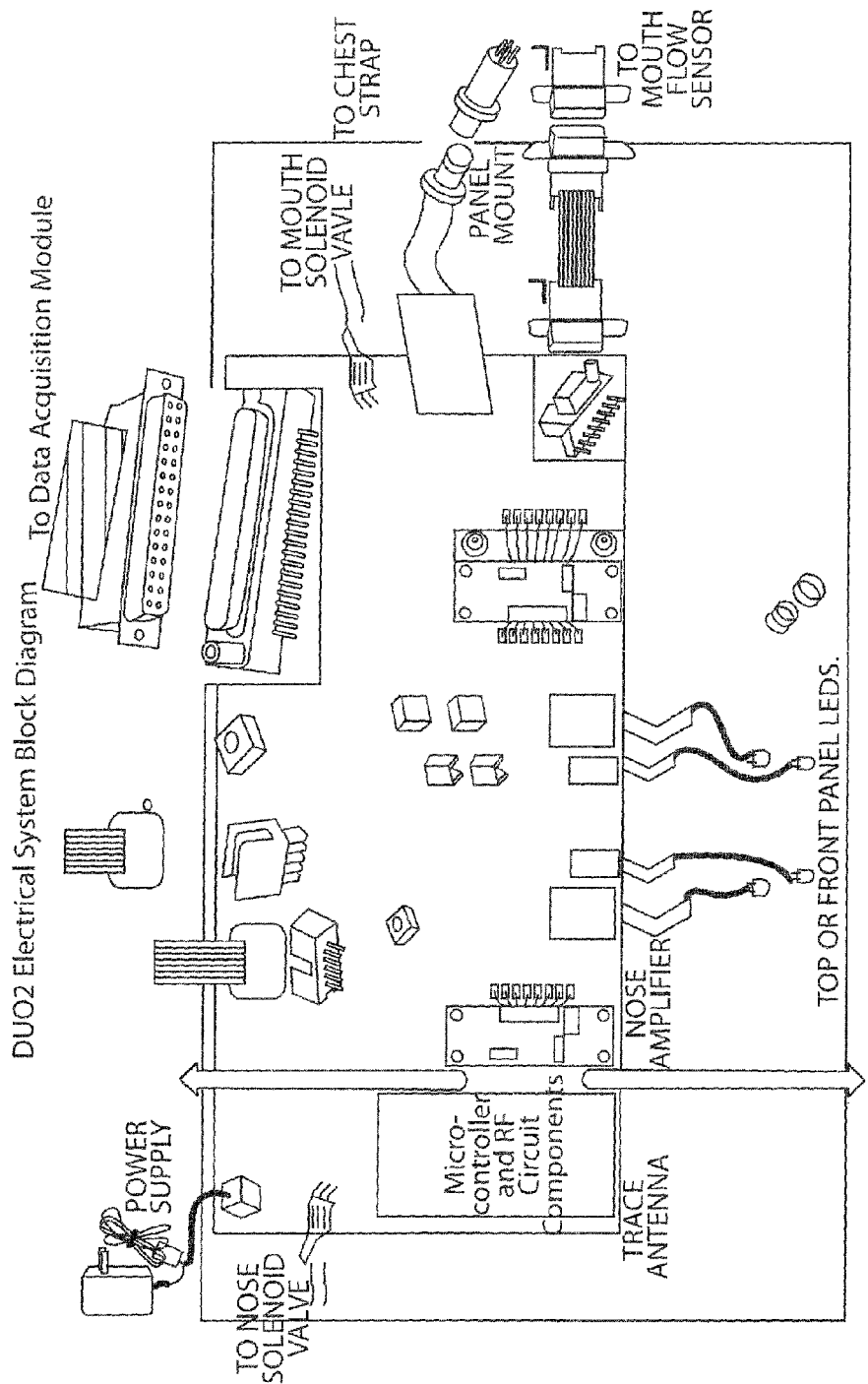
FIG. 9 is a block diagram of a sensor and control in accordance with the present invention which was used to test the nasal flow sensor and time trigger responses.

A circuit diagram of a sensor and control in accordance with the present invention is shown in FIG. 9.

In some cases, some of the flow data may be timed out to avoid double triggering based on a patient's physiologic rate. Other options also are possible.

Although the present invention has been described in detail with reference to certain embodiments, one skilled in the art will appreciate that the present invention can be practiced by other than the described embodiments, which have been presented for purposes of illustration and not of limitation. For example, the above described system may be plugged into a conventional fixed flow regulator, or to a conventional hospital wall unit regulator, and convert same to a "smart regulator". The System also may be built into or adapted as an add-on feature to a C-PAP mask and enable conservation of oxygen. Still other changes are possible. Therefore, the scope of the appended claims should not be limited to the description of the embodiments contained herein.

I claim:

1. A method for controlling delivery of an oxygen enriched gaseous fluid from a source of the fluid to a patient, said method comprising:
   providing a fluid delivery system comprising:
   at least one source of said fluid;
   at least one valve assembly coupled to said at least one source of said fluid, wherein the at least one valve assembly is configured to allow flow of said fluid from the at least one source during patient inspiration;
   an outlet end comprising a nasal or oro-nasal cannula in fluid communication with the at least one valve assembly; and
   a nasal flow sensor configured for sensing nasal flow leakage through a patient's nasal cavity during nasal inhalation as well as to detect nasal flow leakage during mouth inhalation, to determine when inspiration begins, and
   triggering a timed pulse fluid delivery to begin in response to and to continue at least in part during patient inspiration.

2. The method of claim 1, wherein the fluid delivery system further comprises a power source configured to operate the at least one valve assembly.

3. The method of claim 1, wherein the nasal flow sensor is located in or adjacent the nasal cannula or oro-nasal cannula, or is located adjacent the at least one source of fluid, or is located in air tubing between the nasal cannula or oro-nasal cannula and the at least one source of fluid.

4. The method of claim 1, wherein the oro-nasal cannula comprises split nasal cannuli and an oral cannula coupled to each other.

5. The method of claim 4, wherein the nasal cannuli and the oral cannula are coupled to each other by an adjustable length sleeve.

6. The method of claim 4, wherein the split nasal cannuli and the oral cannula are coupled to each other by detachable tubing.

7. The method of claim 4, wherein the split nasal cannuli and the oral cannula are in fluid communication with a shared valve assembly.

8. The method of claim 4, wherein the split nasal cannuli and the oral cannula are each in fluid communication with a separate valve assembly.

9. The method of claim 4, further comprising an oral flow sensor for triggering fluid delivery in response to patient inhalation.

10. The method of claim 1, wherein the at least one valve assembly comprises at least one solenoid valve.

11. The method of claim 1, wherein the fluid delivered comprises supplemental oxygen.

12. The method of claim 1, further comprising circuitry for controlling the at least one valve assembly based on signals from the flow sensor.

13. The method of claim 12, wherein the circuitry comprises a trigger mechanism for actuating the release of fluid through said at least one valve assembly.

14. A method for conserving oxygen being delivered from an enriched oxygen supply to a patient, comprising:
   providing an oxygen conserver controller connected between the oxygen supply and a nasal cannula or an oro-nasal cannula, wherein said controller comprises at least one valve triggered selectively to deliver oxygen to the nasal or oro-nasal cannuli;
   a sensor configured to sense nasal inspiration; and
   a trigger mechanism, communicating with said sensor for actuating the conserver controller, wherein the sensor for sensing patient inhalation is configured to detect flow through a patient's nasal cavity during nasal inhalation as well as to detect nasal flow leakage during mouth inhalation, and
   upon sensing patient inhalation, actuating said conserver controller to open said at least one valve to deliver a pulse of oxygen to said at least one nasal or oro-nasal cannuli during when said patient is inhaling.

15. The method of claim 14, wherein said sensor is selected from the group consisting of an acoustic sensor, a flow sensor, a pressure sensor, a temperature sensor, a carbon dioxide sensor, a strain gauge, and an electromechanical sensor.

16. The method of claim 14, wherein said sensor and said trigger mechanism are remote from one another.

17. The method of claim 14, wherein said sensor and said trigger mechanism communicate either by wire or wirelessly.

18. A method for conserved delivery of an oxygen enriched gaseous fluid to a patient, comprising the steps of:
   providing a valve in communication with a fluid source and a nasal or oro-nasal cannula;
   sensing, with a nasal flow sensor, nasal flow during nasal inspiration and nasal flow leakage that occurs when the patient is mouth breathing; and
   triggering the valve, in response to the sensed inspiration and nasal flow leakage, to begin to release a pulse of fluid from the fluid source for delivery to the patient via the nasal or oro-nasal cannula, and continuing the pulse of fluid at least in part during said patient inspiration.

19. The method of claim 18, wherein the fluid delivered comprises oxygen.

* * * * *

UNITED STATES PATENT AND TRADEMARK OFFICE
CERTIFICATE OF CORRECTION

PATENT NO. : 9,707,366 B2
APPLICATION NO. : 14/476552
DATED : July 18, 2017
INVENTOR(S) : Metelits It is certified that error appears in the above-identified patent and that said Letters Patent is hereby corrected as shown below:

In the Claims

Claim 5, Column 11, Line 57, "the nasal cannuli" should be --the split nasal cannuli--.

Signed and Sealed this
Twenty-third Day of July, 2019

Andrei Iancu
*Director of the United States Patent and Trademark Office*